United States Patent [19]

Natraj et al.

[11] Patent Number: 5,244,665
[45] Date of Patent: Sep. 14, 1993

[54] COSMETIC COMPOSITION

[75] Inventors: Collur V. Natraj; Govindarajan Raman, both of Bombay, India

[73] Assignee: Chesebrough-Pond's USA Co., Division of Conopco, Inc., Greenwich, Conn.

[21] Appl. No.: 879,657

[22] Filed: May 6, 1992

[30] Foreign Application Priority Data

May 7, 1991 [GB] United Kingdom ............... 9109965

[51] Int. Cl.$^5$ .............................................. A61K 6/00
[52] U.S. Cl. ................................... 424/401; 424/59; 514/785
[58] Field of Search .................... 424/401, 59; 514/785

[56] References Cited

U.S. PATENT DOCUMENTS

| | | | |
|---|---|---|---|
| 3,214,338 | 10/1965 | Ehrlich | 514/772.4 |
| 4,515,810 | 5/1985 | Chow et al. | 514/530 |
| 4,847,071 | 7/1989 | Bissett | 424/59 |
| 4,866,202 | 9/1989 | Weil | 560/180 |
| 4,866,203 | 9/1989 | Weil | 514/785 |
| 4,908,389 | 3/1990 | Mahjour et al. | 514/772 |
| 5,047,166 | 9/1991 | Weil | 252/132 |
| 5,089,531 | 2/1992 | Weil | 514/785 |

FOREIGN PATENT DOCUMENTS

| | | |
|---|---|---|
| 0006232 | 1/1980 | European Pat. Off. |
| 0260859 | 3/1988 | European Pat. Off. |
| 0347664 | 12/1989 | European Pat. Off. |
| 0357186 | 3/1990 | European Pat. Off. |
| 2826758 | 12/1979 | Fed. Rep. of Germany |
| 995175 | 6/1965 | United Kingdom |

OTHER PUBLICATIONS

J. Pharmaceutical Sciences (1974), vol. 63, pp. 1376-1379.
Chemical Abstracts 114:30149V for JP 02140167.
Chemical Abstracts 100:39448K for JP 58180417.
Patent Abstract of Japan, vol. 13, No. 199 (11 May 1989) and JP-A-1 019 012 (Kenebo) (23 Jan. 1989).
European Search Report.

Primary Examiner—Thurman K. Page
Assistant Examiner—William E. Benston
Attorney, Agent, or Firm—Milton L. Honig

[57] ABSTRACT

A composition suitable for topical application to human skin for reducing the damaging effects of ultra-violet light on skin comprises:

(a) an effective amount of a triester of citric acid having the structure (1):

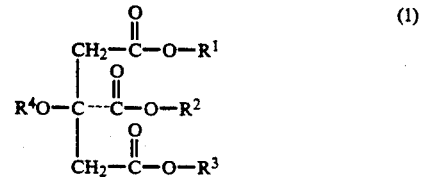

where $R^1$, $R^2$, and $R^3$ each independently represent a branched or unbranched alkyl, alkenyl, aryl, alkylaryl or arylalkyl group, each said group being optionally substituted and having from 1 to 18 carbon atoms, $R^4$ represents —H, or a branched or unbranched saturated or unsaturated acyl, alkyl, aryl, alkylaryl or arylalkyl group, each said group being optionally substituted and having from 1 to 18 carbon atoms; and (b) a cosmetically acceptable vehicle for the citric acid ester; and (c) an effective amount of a sunscreen agent, with the proviso that in the case where the sunscreen agent is an inorganic sunscreen, it has an average particle size of less than 100 μm.

10 Claims, No Drawings

COSMETIC COMPOSITION

FIELD OF INVENTION

The invention relates to a composition for topical application to human skin in order to promote the repair of photo-damaged skin and/or to reduce or prevent the damaging effects of ultra-violet light on skin. The invention also relates to the use of such compositions in the repair of photo-damaged skin and in the prevention of damage to skin due to exposure to ultra-violet light.

BACKGROUND TO THE INVENTION

The treatment of human skin damaged due to exposure to ultra-violet light, i.e. photo-damage, has been subject to much research effort in recent years, particularly with the realisation that skin cancer and other skin disorders can arise where the exposure to sunlight is excessive. This problem is even more serious with the depletion of the ozone layer which is believed to permit a higher level of ultra-violet radiation to reach the earth's surface.

Chronic exposure to sunlight results in multiple adverse effects on all structural elements of the skin. The clinical manifestation of these changes, collectively known as photoageing is lax, dry inelastic skin that is wrinkled and blotchy with a coarse, roughened texture.

Skin blotchiness or mottling (hyperpigmentation) which accompanies photo-ageing results from changes in the melanocytes within the population of epidermal cells. These pigment producing cells, which unlike the keratinocytes remain at the base of the epidermis, lose their normal regulation process with ageing and produce excess pigment. This leads to the formation of dense perinuclear clumps of melanin in slowly turning over keratinocytes within the epidermis, and areas of hyperpigmentation or 'age spots' develop.

In the therapy of such hyperpigmented skin, certain skin lightening agents such as kojic acid, hydroquinone or ascorbic acid are effective by inhibiting the formation of melanin. Vitamin A acid (retinoic acid) is beneficial in hyperpigmentation problems by normalising the melanocyte population.

Also by increasing cell turnover, Vitamin A acid prevents accumulation of pigment within the more rapidly dividing and migrating keratinocytes. Vitamin A acid also enhances the pigment reducing potential of conventional skin lightening agents.

The topical application of Vitamin A acid does however have a major drawback in that it is a skin irritant, and can accordingly damage the skin. Its recommended use for example as a prescription drug in the treatment of acne involves careful control, such that excessive doses are avoided in order to restrict the side effects which can occur with skin. By the same token, the use of Vitamin A acid in the treatment or prevention of photo-damaged skin is severely limited by these side effects.

In an attempt to overcome this problem and as a result of a programme of screening substances other than retinoic acid for their ability to treat or prevent photo-damage of skin, without the aforementioned side effects, we have discovered that certain esters of citric acid, especially tributyl citrate are particularly effective in this respect. Use of such esters is advantageous since they have a history of safe use, for example as plasticizers, including in plastics as used in intravenous fluid tubings.

The invention is accordingly concerned with the use of esters of citric acid in the treatment of photo-damaged and/or hyperpigmented skin, and in slowing down the ageing process generally. The invention also concerns compositions for topical application to human skin to reduce damaging effects of ultra-violet light on skin, comprising a citric acid esters in combination with a sunscreen material.

DEFINITION OF THE INVENTION

Accordingly, in one aspect, the invention provides a composition suitable for topical application to human skin in order to reduce the damaging effects of ultra-violet light on skin, which composition comprises:

(a) an effective amount of a triester of citric acid having the structure (1):

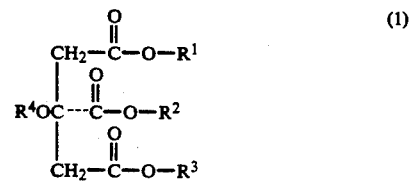

where
R$^1$, R$^2$ and R$^3$ each independently represent a branched or unbranched alkyl, alkenyl, aryl, alkylaryl or arylalkyl group, each said group being optionally substituted and having from 1 to 18 carbon atoms, R$^4$ represents —H, or a branched or unbranched saturated or unsaturated acyl, alkyl, aryl, alkylaryl or arylalkyl group, each said group being optionally substituted and having from 1 to 18 carbon atoms; and (b) a cosmetically acceptable vehicle for the citric acid ester; and (c) an effective amount of a sunscreen agent, with the proviso that in the case where the sunscreen agent is an inorganic sunscreen, it has an average particle size of less than 100 μm.

In another aspect the present invention provides use of a triester of citric acid having the structure (1) as defined above as an agent for reducing the damaging effects of ultraviolet light on skin, in a topical composition comprising a major proportion of a cosmetically acceptable vehicle for the ester of citric acid.

DISCLOSURE OF THE INVENTION

The invention concerns a composition comprising an organic ester of citric acid, together with a suitable cosmetically acceptable vehicle and a sunscreen agent, which acts to retard the ageing process of the skin, when applied topically thereto. The sunscreen agent in the composition assists to prevent skin blotchiness and mottling due to hyperpigmentation and generally effect an overall improvement in skin texture with reduction in fine wrinkling and improved skin colour. Co-formulation with a sunscreen is also believed to enhance synergistically the photo-stability and activity of the ester of citric acid within the formulation and also prevent further actinic damage to all epidermal cells and dermal tissue.

The ester of citric acid

The composition according to the invention comprises a triester of citric acid or mixtures thereof, each having the structure (1).

The preferred esters of citric acid are those where the $R^1$, $R^2$ and $R^3$ groups in structure (1) are each alkyl groups, examples of which include:
trimethyl citrate;
triethyl citrate;
tri-n-propyl citrate;
tri-n-butyl citrate;
trihexyl citrate;
trioctyl citrate;
tridodecyl citrate;
trihexadecyl citrate;
triphenyl citrate;
tri-2-ethylhexyl citrate.

Typically $R^1$, $R^2$ and $R^3$ are alkyl groups, preferably unsubstituted, having from 1 to 12 carbon atoms, particularly 1 to 8, and most preferably 4 to 6 carbon atoms. It is also preferred that $R^1 = R^2 = R^3$.

The above preferred trialkyl citrates can also be acylated at the 2 position, further to enhance their lipophilic character, and examples of these are:
2-acetyl trimethyl citrate;
2-acetyl triethyl citrate;
2-acetyl tri-n-propyl citrate;
2-acetyl tri-n-butyl citrate;
2-oleoyl tri-n-butyl citrate;
2-O-methyl tri-n-butyl citrate;
2-O-ethyl tri-n-butyl citrate;
2-O-isopropyl tri-n-butyl citrate.

The most preferred citrates are those in which $R^4$ is an acyl group having from 2 to 4 carbon atoms, or an alkyl group having from 1 to 4 carbon atoms.

The most preferred ester of citric acid is tri-n-butyl citrate or its acylated derivative.

The amount of the ester of citric acid having the structure (1), present in the composition according to the invention is from 0.01 to 20%, particularly from 0.1 to 10% by weight of the composition, preferably more than 0.5%, most preferably at least 1% and typically less than 6%.

The Cosmetically Acceptable Vehicle

The composition according to the invention also comprises a cosmetically acceptable vehicle to act as a dilutant, dispersant or carrier for other materials present in the composition, so as to facilitate their distribution when the composition is applied to the skin.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, isopropanol, acetone, ethylene glycol monoethyl ether, diethylene glycol monobutyl ether, diethylene glycol monoethyl ether;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

Organic sunscreens

The composition of the invention includes an effective amount of a sunscreen agent which may comprise an organic sunscreen further to enhance synergistically the benefit of the composition in providing protection from the harmful effects of excessive exposure to sunlight.

Examples of suitable organic sunscreens, when required, include those set out in Table 1 below, and mixtures thereof.

TABLE 1

| CTFA Name | Trade Name | Supplier |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenyl-benzimidazole--5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |

TABLE 1-continued

| CTFA Name | Trade Name | Supplier |
| --- | --- | --- |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |
| — | PONGAMOL | — |

The composition of the invention can accordingly comprise from 0.1 to 10%, preferably from 1 to 5%, suitably 1.5 to 4.5% by weight of an organic sunscreen material.

Inorganic sunscreen

The sunscreen agent according to the invention can optionally comprise an inorganic sunscreen, such as ultrafine titanium dioxide in either of two forms, namely water-dispersible titanium dioxide and oil-dispersible titanium dioxide.

Water-dispersible titanium dioxide is ultrafine titanium dioxide, the particles of which are uncoated or which are coated with a material to impart a hydrophilic surface property to the particles. Examples of such materials include aluminium oxide and aluminium silicate.

Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably 70 nm or less, more preferably from 10 to 40 nm and most preferably from 15 to 25 nm.

By topical application to the skin of a mixture of both water-dispersible ultrafine titanium dioxide and oil-dispersible ultrafine titanium dioxide, synergistically enhanced protection of the skin against the harmful effects of both UV-A and UV-B rays is achievable.

It is believed that this unexpected benefit is due to the deposition of each type of titanium dioxide on different regions of the skin surface, water-dispersible titanium dioxide being preferentially retained by hydrophilic regions of the skin's surface, while oil-dispersible titanium dioxide is retained preferentially by hydrophobic regions of the skin's surface. The combined overall effect is that more efficient physical coverage of the skin's surface is attainable and this can be demonstrated by measurement of the Sun Protection Factor (SPF).

In order to achieve the enhanced, synergistic benefit, as herein described, the weight ratio of water-dispersible titanium dioxide to oil-dispersible titanium dioxide should be from 1:4 to 4:1, preferably from 1:2 to 2:1 and ideally about equal weight proportions.

The total amount of titanium dioxide that can optionally can be incorporated in the composition according to the invention is from 1 to 25%, preferably from 2 to 10% and ideally from 3 to 7% by weight of the composition.

Other Inorganic Sunscreens

The emulsion of the invention optionally can comprise an inorganic sunscreen in addition to ultrafine titanium dioxide as herein defined. Preferably the inorganic sunscreen has an average particle size of less then 70 nm, preferably from 10 to 40 nm and most preferably from 15 to 25 nm.

Examples of other inorganic sunscreens include: zinc oxide, iron oxide, and silica, such as fumed silica, having an average particle size of less than 100 nm, typically from 1 nm to 100 nm.

It should be noted that silica, when used as an ingredient in the emulsion according to the invention can provide protection from infra-red radiation. Suitably the composition includes from 1 to 25%, typically from 2 to 10% and most preferably from 3 to 7% by weight of inorganic sunscreens.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or oily material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

Oily vehicles in which the esters are soluble or miscible, such that a composition is formed which does not separate into two or more phases on standing are particularly advantageous. In such compositions penetration of the citric acid ester into the skin can thereby be expected to be enhanced.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLC value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 | 18.7 |

TABLE 1-continued

| Chemical Name of Emulsifier | Trade Name | HLB Value |
|---|---|---|
| | MS | |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, that optionally can be incorporated in the composition of the invention is from 1 to 50%, preferably from 2 to 20% and most preferably from 2 to 10% by weight of the composition.

Water

The composition of the invention can also comprises water, usually up to 80%, preferably from 5 to 80% by volume.

Silicone Surfactant

The composition of the invention can also optionally comprises a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

$$CH_3-\underset{\underset{CH_3}{|}}{\overset{\overset{CH_3}{|}}{Si}}-O-\left[\underset{\underset{R^1}{|}}{\overset{\overset{CH_3}{|}}{Si}}-O\right]_x-\left[\underset{\underset{R''}{|}}{\overset{\overset{CH_3}{|}}{Si}}-O\right]_y-\underset{\underset{CH_3}{|}}{\overset{\overset{CH_3}{|}}{Si}}-CH_2$$

where the groups R' and R" are each chosen from —H, $C_{1-18}$ alkyl and $$-[CH_2CH_2O]_a[CH_2\underset{\underset{CH_3}{|}}{CHO}]_bH$$

a has a value of from 9 to 115,
b has a value of from 0 to 50,
x has a value of from 133 to 673,
y has a value of from 25 to 0.25
Preferably, the dimethyl polysiloxane polymer is one in which:
a has a value of from 10 to 114,
b has a value of from 0 to 49,
x has a value of from 388 to 402,
y has a value of from 15 to 0.75.
one of groups R' and R" being lauryl, and the other having a molecular weight of from 1000 to 5000.

A particularly preferred dimethyl polysiloxane polymer is one in which:
a has the value 14,
b has the value 13,
x has the value 249;
y has the value 1.25.

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Retinol and derivatives thereof

The composition according to the invention optionally can also comprise an additional anti-ageing active such as retinol (Vitamin A) and/or derivative thereof, further to enhance repair of photo damage to skin following exposure to ultra-violet light.

In addition to retinol itself, examples of derivatives of retinol include:
Retinyl acetate,
Retinyl butyrate,
Retinyl propionate,
Retinyl octanoate,
Retinyl laurate,
Retinyl palmitate,
Retinyl oleate, and
Retinyl linoleate.

The amount of retinol, or a cosmetically acceptable derivative thereof, when present in the composition according to the invention is from 0.01 to 10% and preferably 0.1 to 5% by weight of the composition.

Tocopherol

The composition according to the invention optionally can also comprise a tocopherol (vitamin E group), as an antioxidant for retinol, or a derivative, when present in the composition, and to limit oxidative damage to skin. The vitamin E group comprises $\alpha$-tocopherol, $\beta$-tocopherol, $\alpha$-tocopherol, and $\delta$-tocopherol.

The amount of a tocopherol, when present in the composition according to the invention, is from 0.0001 to 20%, preferably from 0.001 to 10% by weight of the composition.

Other Cosmetic Adjuncts

Examples of conventional adjuncts which can optionally be employed include preservatives, such as parahydroxy benzoate esters; antioxidants, such butyl hydroxy toluene; humectants, such as glycerol, sorbitol, 2-pyrrolidone-5-carboxylate, dibutylphthalate, gelatin, polyethylene glycol, such as PEG 200-600; buffers, such as lactic acid together with a base such as triethanolamine or sodium hydroxide; waxes, such as beeswax, ozokerite wax, paraffin wax; plant extracts, such as Aloe vera, cornflower, witch hazel, elderflower, cucumber; thickeners; activity enhancers; colourants; and perfumes. Cosmetic adjuncts can form the balance of the composition.

Use of the Composition

The composition according to the invention is intended primarily as a skin care product for topical application to human skin to prevent photo-damage to skin, which can result from exposure to sunlight, and which can retard natural skin ageing. The composition can also be used to reduce skin blotchiness and mottling due to hyperpigmentation, to improve skin texture with reduction in fine wrinkling and otherwise to improve skin colour and texture. In general, the composition, when topically applied to skin, is useful in the prevention of actinic damage to all epidermal cells and dermal tissue.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer.

For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined. Evidence to demonstrate the effectiveness of tri-n-butyl citrate when applied to skin A base composition (cream) was prepared as a vehicle for retinoic acid, retinol or tri-n-butyl citrate, to study changes to skin, if any, attributable to these substances.

The base composition (cream) contained the following ingredients:

| Ingredients | % (w/w) |
| --- | --- |
| Stearic acid | 18 |
| Cetostearyl alcohol | 0.5 |
| Glycerine | 1 |
| Dimethicone | 0.2 |
| Minor ingredients | 5 |
| Water | to 100 |

Test creams were then prepared by addition to the base cream of retinoic acid, retinol or tri-n-butyl citrate. The test and control (i.e. no additives) creams were applied to the depilated backs of albino mice, albino guinea pigs and black mice (50 mg per animal per application). A total of from 4 to 30 applications were made. Evaluations were performed at the end of the treatment periods by gross morphology and microscopic anatomy. The results re tabulated below:

| Creams | Results |
| --- | --- |
| 1. Placebo | No effects |
| 2. 0.05% Retinol | Epidermal thickness increased but stratum corneum not affected. |
| 3. 0.05% Retinoic acid | As for retinol but marked irritation and scaling seen. |

| Creams | Results |
| --- | --- |
| 4. 2% Tributyl citrate | As for retinol |

Conclusions

Tri-n-butyl citrate caused histological changes in the epidermis that were similar to that caused by retinol. This indicates that the effects would be beneficial and that tri-n-butyl citrate would have antiageing properties. No irritant effects were observed even on prolonged application.

EXAMPLES

The invention is further illustrated by the following examples; in each formulation, the titanium dioxide employed was ultrafine titanium dioxide having a mean particle size of from 15 to 25 nm.

Example 1

This example illustrates a lotion according to the invention.

| Ingredient | % w/w |
| --- | --- |
| tri-n-butyl citrate | 2 |
| silicone surfactant | 10 |
| volatile siloxane | 14 |
| mineral oil | 1.5 |
| titanium dioxide (water-dispersible) | 2.5 |
| titanium dioxide (oil-dispersible) | 2.5 |
| 2-hydroxy octanoic acid | 1 |
| 2-hydroxy propanoic acid | 5 |
| butylene glycol | 10 |
| sodium chloride | 2 |
| 1-proline | 0.1 |
| neutralising agent | qs |
| preservative | qs |
| perfume | qs |
| water | qs |

Example 2

This example illustrates a fluid cream according to the invention.

| Ingredient | % w/w |
| --- | --- |
| tri-n-propyl citrate | 3 |
| volatile siloxane (DC 345) | 8.2 |
| silicone surfactant (DC 3225C) | 12 |
| petroleum jelly | 0.5 |
| mineral oil | 1.5 |
| Parsol MCX (octyl methoxycinnamate) | 3 |
| titanium dioxide (oil-dispersible) | 2 |
| titanium dioxide (water-dispersible) | 2 |
| sodium chloride | 2 |
| butylene glycol | 10 |
| 1-proline | 0.1 |
| 2-hydroxy octanoic acid | 1 |
| 2-hydroxy propanoic acid | 5 |
| neutralising agent | qs |
| preservative | qs |
| perfume | qs |
| water | qs |

Example 3

This example illustrates a cream according to the invention.

| Ingredient | % w/w |
| --- | --- |
| triphenyl citrate | 2 |
| volatile siloxane (DC 345 Fluid) | 8.2 |
| silicone surfactant (DC 3225C) | 12 |
| mineral oil | 1.5 |
| petroleum jelly | 0.5 |
| Parsol MCX (octyl methoxycinnamate) | 1.5 |
| titanium dioxide (oil-dispersible) | 1.0 |
| titanium dioxide (water-dispersible) | 1 |
| 2-hydroxyoctanoic acid | 1 |
| 2-hydroxypropanoic acid | 5 |
| sodium chloride | 2 |
| butylene glycol | 10 |
| 1-proline | 0.1 |
| neutralising agent (aqueous phase to 4.5) | q.s. |
| preservative | q.s. |
| perfume | q.s. |
| water | to 100 |

Example 4

This example illustrates a lotion according to the invention.

| Ingredient | % w/w |
| --- | --- |
| trioctyl citrate | 1 |
| silicone surfactant (DC 3225C) | 10 |
| volatile siloxane (DC 345) | 14 |
| mineral oil | 1.5 |
| Parsol MCX | 3 |
| titanium dioxide (oil-dispersible) | 2 |
| titanium dioxide (water-dispersible) | 2 |
| butylene glycol | 10 |
| sodium chloride | 2 |
| 1-proline | 0.1 |
| 2-hydroxy octanoic acid | 1 |
| 2-hydroxy propanoic acid | 5 |
| neutralising agent | qs |
| perfume | qs |
| preservative | qs |
| water | qs |

Example 5

This example illustrates a cream in accordance with the invention.

| Ingredient | % w/w |
| --- | --- |
| tri-n-butyl citrate | 2 |
| trimethyl citrate | 1 |
| Polyoxyethylene (2) stearyl alcohol | 3 |
| Polyoxyethylene (21) stearyl alcohol | 2 |
| cetyl alcohol | 1.5 |
| soft white paraffin | 1.5 |
| silicone fluid 200 | 5 |
| liquid paraffin | 8 |
| glycerin | 2 |
| preservatives | 0.5 |
| titanium dioxide (water-dispersible) | 2.5 |
| titanium dioxide (oil-dispersible) | 2.5 |
| water | to 100 |

Example 6

This example also illustrates a cream in accordance with the invention.

| Ingredients | % w/w |
| --- | --- |
| triethyl citrate | 2 |
| tri-n-butyl citrate | 2 |
| cetyl dimethicone copolyol | |

| Ingredients | % w/w |
|---|---|
| cetyl dimethicone polyglyceryl-3-oleate hexyl laurate | 5 |
| isopropyl myristate | 13.5 |
| beeswax | 3 |
| silicone fluid 200 | 5 |
| preservatives | 0.5 |
| titanium dioxide (water-dispersible) | 2.5 |
| titanium dioxide (oil-dispersible) | 2.5 |
| water | to 100 |

*Available is ABIL W508 ex Goldschmidt

Example 7

This example illustrates a lotion according to the invention. 1

| Ingredient | % w/w |
|---|---|
| 2-acetyl tri-n-butyl citrate | 2 |
| silicone surfactant | 10 |
| volatile siloxane | 14 |
| mineral oil | 1.5 |
| ultrafine titanium dioxide (water-dispersible) | 5 |
| 2-hydroxy octanoic acid | 1 |
| 2-hydroxy propanoic acid | 5 |
| butylene glycol | 10 |
| sodium chloride | 2 |
| amino acid | 0.1 |
| neutralising agent | qs |
| preservative | qs |
| perfume | qs |
| water | qs |

Example 8

This example illustrates a lotion according to the invention.

| Ingredient | % w/w |
|---|---|
| 2-0-ethyl tri-n-butyl citrate | 3 |
| silicone surfactant | 10 |
| volatile siloxane | 14 |
| mineral oil | 1.5 |
| ultrafine titanium dioxide (oil-dispersible) | 5 |
| 2-hydroxy octanoic acid | 1 |
| 2-hydroxy propanoic acid | 5 |
| butylene glycol | 10 |
| sodium chloride | 2 |
| amino acid | 0.1 |
| neutralising agent | qs |
| preservative | qs |
| perfume | qs |
| water | qs |

Example 9

This example illustrates a lotion according to the invention.

| Ingredient | % w/w |
|---|---|
| tridodecyl citrate | 1 |
| silicone surfactant | 10 |
| volatile siloxane | 14 |
| mineral oil | 1.5 |
| ultrafine titanium dioxide (water-dispersible) | 2.5 |
| ultrafine titanium dioxide (oil-dispersible) | 2.50 |
| 2-hydroxy octanoic acid | 1 |
| 2-hydroxy propanoic acid | 5 |
| butylene glycol | 10 |
| sodium chloride | 2 |
| amino acid | 0.1 |
| neutralising agent | qs |
| preservative | qs |
| perfume | qs |
| water | qs |

Example 10

This example illustrates an anhydrous formulation for addition of sunscreen in accordance with the invention.

| Ingredient | % w/w |
|---|---|
| tri-n-butyl citrate | 5 |
| Iso-propyl alcohol | 10 |
| ethyl hexyl palmitate | 8.7 |
| antioxidant | 0.1 |
| volatile silicone | to 100 |

We claim:

1. A composition suitable for topical application to human skin in order to reduce the damaging effects of ultra-violet light on skin, which composition comprises:
   (a) from 0.01 to 20% of a triester of citric acid having the structure (1):

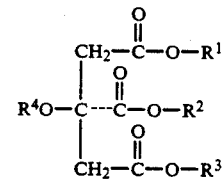

where
$R^1$, $R^2$ and $R^3$ each independently represent a branched or unbranched alkyl, alkenyl, aryl, alkylaryl or arylalkyl group, each said group being optionally substituted and having from 1 to 18 carbon atoms, $R^4$ represents —H, or a branched or unbranched saturated or unsaturated acyl, alkyl, aryl, alkylaryl or arylalkyl group, each said group being optionally substituted and having from 1 to 18 carbon atoms; and (b) a cosmetically acceptable vehicle for the citric ester present in an effective amount to facilitate distribution of the ester when the composition is applied to the skin; and
   (c) from 0.1 to 25% of a sunscreen agent which is an organic or inorganic sunscreen, with the proviso that in the case where the sunscreen agent is an inorganic sunscreen, it has an average particle size of less than 100 μm.

2. A composition according to claim 1, wherein $R^1$, $R^2$, and $R^3$ are unsubstituted alkyl groups having from 1 to 8 carbon atoms.

3. A composition according to claim 1 wherein the ester of citric acid is tri-n-butyl citrate.

4. A composition according to claim 1 wherein $R^4$ is selected from the groups consisting of an acyl group having from 2 to 4 carbon atoms and an alkyl group having from 1 to 4 carbon atoms.

5. A composition according to claim 1 comprising from 0.1 to 10% of an organic sunscreen material.

6. A composition according to claim 1 comprising from 1 to 25% of an inorganic sunscreen material.

7. A composition according to claim 6 wherein the inorganic sunscreen comprises a mixture of water-dispersible and oil-dispersible titanium dioxide.

8. A composition according to claim 7 wherein the titanium dioxide has a mean particle size of from 15 to 25 nm.

9. A method for reducing the damaging effects of ultra-violet light on skin comprising topically applying to the skin a composition comprising:

(a) from 0.1 to 20% of a triester of citric acid having the structure (1):

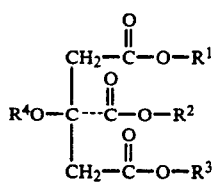

where $R^1$, $R^2$ and $R^3$ each independently represent a branched or unbranched alkyl, alkenyl, aryl, alkylaryl or arylalkyl group, each said group being optionally substituted and having from 1 to 18 carbon atoms.

$R^4$ represents —H, or a branched or unbranched saturated or unsaturated acryl, arlkyl, aryl, alkylaryl or arylalkyl group, each said group being optionally substituted and having from 1 to 18 carbon atoms; and (b) a cosmetically acceptable vehicle for the citric ester present in an effective amount to facilitate distribution of the ester when the composition is applied to the skin; and (c) from 0.1 to 25% of a sunscreen agent which is an organic or inorganic suns screen, with the proviso that in the case where the sunscreen agent is an inorganic sunscreen, it has an average particle size of less than 100 μm.

10. A method according to claim 9 wherein the ester of citric acid is tri-n-butyl citrate.

* * * * *